US00PP13687P29

(12) United States Plant Patent
Zaiger et al.

(10) Patent No.: US PP13,687 P2
(45) Date of Patent: Mar. 25, 2003

(54) INTERSPECIFIC TREE NAME 'SIERRA ROSE'

(76) Inventors: Gary Neil Zaiger, 1907 Elm Ave., Modesto, CA (US) 95358; Leith Marie Gardner, 4005 California Ave., Modesto, CA (US) 95358; Grant Gene Zaiger, 1207 Grimes Ave., Modesto, CA (US) 95358

( * ) Notice: Subject to any disclaimer, the term of this patent is extended or adjusted under 35 U.S.C. 154(b) by 0 days.

(21) Appl. No.: 10/120,530

(22) Filed: Apr. 11, 2002

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Anne Marie Grünberg

(57) ABSTRACT

A new and distinct variety of interspecific tree [(Plum×Plumcot)×((Apricot×Plumcot)×apricot)]. The following features of the tree and its fruit are characterized with the tree budded on 'Citation' Rootstock (U.S. Plant Pat. No. 5,112), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features:

1. Fruit with excellent eating quality.
2. Vigorous, upright growth.
3. Fruit with a high degree of attractive brownish violet color.
4. Fruit having firm flesh with good handling and storage quality.
5. Fruit with high Brix, (soluble solids), average 16°.

1 Drawing Sheet

BACKGROUND OF THE VARIETY

Field of the Invention

In the field of plant genetics, we conduct an extensive and continuing plant-breeding program including the organization and asexual reproduction of orchard trees, and of which almonds, apples, plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of plum trees (*Prunus salicina*) and apricot trees (*Prunus armeniaca*), which are known to us, and mentioned herein, are 'Friar' Plum (non-patented), 'Autumn Giant' Plum (U.S. Plant Pat. No. 5,624), 'Modesto' Apricot (U.S. Plant Pat. No. 2,543) and the Interspecific tree 'Citation' (U.S. Plant Pat. No. 5,112), (*Prunus salicina*)×(*Prunus persica*).

STATEMENT REGARDING FEDERALLY SPONSORED RESEARCH OR DEVELOPMENT

Not applicable.

ORIGIN OF THE VARIETY

The present new and distinct variety of interspecific (Prunus) tree was developed by us in our experimental orchard as a first generation cross between two proprietary lines of immediate parents with field identification numbers 326LC131 and 391LD449. The parentage of the maternal parent (326LC131) was derived from various crosses with the following parents, 'Friar' Plum (non-patented), 'Autumn Giant' Plum (U.S. Plant Pat. No. 5,624) and a proprietary plumcot seedling. The pollen parent (391LD449) was developed from the proprietors interspecific seedling derived from 'Modesto' Apricot (U.S. Plant Pat. No. 2,543) crossed with a plumcot, which was crossed with an apricot of unknown parentage. We grew a large number of these first generation seedlings on their own root system. In 1995, we selected bud wood from the most vigorous seedlings and budded these to 'Citation' Rootstock (U.S. Plant Pat. No. 5,112). It was from these budded trees that we recognized the outstanding fruit characteristics of the present variety and selected it for additional asexual reproduction and commercialization.

ASEXUAL REPRODUCTION OF THE VARIETY

Asexual reproduction, performed in 1997, of the new and distinct variety of interspecific tree by budding to 'Citation' Rootstock (U.S. Plant Pat. No. 5,112), as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

Our new and distinct variety of interspecific Prunus tree [(Plum×Plumcot)×((Apricot×Plumcot)×Apricot)] is of large size, vigorous upright growth and is a productive and regular bearer of large, firm, yellow flesh, clingstone fruit with excellent flavor and eating quality. The fruit is further characterized by holding firm on the tree 8 to 10 days after maturity (shipping ripe) and having good storage and shipping quality. The large, relatively uniform fruit throughout the tree has an attractive brownish violet skin color and has high soluble solids, 16° Brix. In comparison to the fruit of 'Friar' Plum (non-patented), the fruit of the new variety is more globose in shape compared to oblate in shape, has a lighter skin color and is approximately 20 days later in maturity. In comparison to the 'Autumn Giant' Plum (U.S. Plant Pat. No. 5,624), the new variety is also more globose compared to cordate shape, is brownish violet in color, compared to red, and is approximately 35 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old trees grown near Modesto, Calif., with color in accordance with Munsell Book of Color.

Tree:

*Size.*—Large. Usually pruned to 3 to 3.5 meters in height for economical harvesting of fruit.

*Growth.*—Vigorous. Tree growth of 1.5 to 2 meters in height the first growing season. Usually pruned the first dormant season and primary scaffolds are selected.

*Form.*—Upright. Usually pruned to vase shape.

*Branching habit.*—Upright. Crotch angle approximately 30°, increases with heavy crop load.

*Productivity.*—Good. Usually thinning and spacing of fruit necessary. Varies slightly with climatic conditions at blooming time.

*Bearer.*—Regular. Tree has set adequate amount of fruit 3 consecutive years. No alternate bearing observed.

*Fertility.*—Self-sterile, pollenizer required.

*Density.*—Medium dense. Usually pruned to vase shape by removing branches from center of tree for increased sunlight and air movement to enhance fruit color and growth of fruitwood.

*Hardiness.*—Hardy in all stone fruit growing areas of California. Tree grown in USDA Hardiness Zone 9. Winter chilling requirement is approximately 600 hours below 45° F.

Trunk:

*Size.*—Large. Circumference of 50.8 cm measured at 29.2 cm above ground on 5 year old tree.

*Surface texture.*—Medium shaggy, increases with age of tree.

*Color.*—5YR 6/2 to 10YR 7/2.

Branches:

*Size.*—Medium. Average circumference 15.2 cm at 1 meter above ground.

*Surface texture.*—Varies from smooth on new growth to medium rough on mature growth. Roughness increases with age.

*Lenticels.*—Average number 58 in 25.8 square cm surface. Average length 3.4 mm. Average width 1.1 mm. Color 2.5YR 7/12.

*Color.*—First years growth varies from 7.5Y 7/10 to 7.5YR 6/10. Older growth varies from 10YR 4/4 to 10YR 4/6, varies with age of growth.

Leaves:

*Size.*—Medium. Average length 95.4 mm. Average width 43.5 mm.

*Form.*—Elliptic.

*Apex.*—Acuminate.

*Base.*—Cuneate.

*Margin.*—Serrate.

*Thickness.*—Medium.

*Surface.*—Upper surface relatively smooth, slightly indented over midrib and leaf veins, glabrous. Lower surface relatively smooth, small ridges created by midrib and pinnate venation, glabrous.

*Petiole.*—Average length 15.7 mm. Average width 1.6 mm. Color 5GY 8/4. Grooved longitudinally, glabrous.

*Glands.*—Globose. Size — small. Average length 0.7 mm. Average diameter 0.6 mm. Number varies from 1 to 4, average number 3. Located on upper portion of petiole and lower part of leaf blade. Color 5GY 8/6. Dirt collecting on sticky substance secreted by leaf glands creates dark appearance.

*Color.*—Upper surface 5GY 4/6. Lower surface 5GY 5/4. Midrib color 5GY 9/4.

Flower buds:

*Size.*—Small. Average length 7.1 mm. Average diameter 3.8 mm.

*Hardiness.*—Hardy in all stone fruit growing areas of California. Grown in USDA Hardiness Zone 9.

*Form.*—Conical, becoming slightly elongated before opening.

*Pedicel.*—Average length 5.3 mm. Average width 0.9 mm. Color 2.5GY 8/4.

*Number of buds per spur.*—Varies from 2 to 24. Average number 6.

*Color.*—N 9/0.5.

Flowers:

*Size.*—Small. Average height 8.4 mm. Average width 16.4 mm.

*Petals.*—Obovate, narrows at point of attachment. Number — 5, alternately arranged to sepals. Average length 7.4 mm. Average width 6.5 mm. Color N 9/0.5. Margin — entire, slightly cupped. Both surfaces glabrous.

*Sepals.*—Shape — ovate, apex rounded. Number — 5, alternately arranged to petals. Both inner and outer surfaces glabrous. Average length 1.6 mm. Average width 1.46 mm. Color — Upper surface 2.5GY 8/6. Lower surface 2.5GY 7/6.

*Stamens.*—Average number per flower — 43. Average filament length 6 mm. Filament color N 9/0.5. Color of anthers 10YR 8/8.

*Pollen.*—Abundant. Self-sterile, pollenizer required. Color 10YR 8/6.

*Pistil.*—Normally 1. Surface glabrous. Average length 5.7 mm. Stigma height compared to anthers is lower by approximately 1.4 mm. Color 2.5Y 8.5/2.

*Fragrance.*—Wanting.

*Blooming period.*—Date of First Bloom Feb. 19, 2001. Date of Petal Fall Mar. 3, 2001. Varies slightly with climatic conditions at blooming time.

*Color.*—N 9/0.5.

*Number of flowers per bud.*—Average 2.

*Pedicel.*—Average length 6.8 mm. Average width 0.93 mm. Color 2.5GY 8/4.

Fruit:

*Maturity when described.*—Firm ripe.

*Date of first picking.*—Aug. 14, 2001.

*Date of last picking.*—Aug. 20, 2001. Varies slightly with climatic conditions.

*Size.*—Large. Average diameter axially 64.5 mm. Average transversely in suture plane 58.2 mm. Average weight 198.4 grams. Average weight varies slightly with fertility of the soil, amount of thinning and climatic conditions.

*Form.*—Nearly globose, slightly retuse at apex and base.

*Suture.*—Shallow, extends from base to apex.

*Ventral surface.*—Sightly lipped. Narrow, creating a distinct suture line.

*Apex.*—Usually slightly flattened to recessed.

*Base.*—Retuse.

*Cavity.*—Rounded to slightly elongated in the suture plane. Average depth 5.6 mm. Average breadth 8.3 mm.

Stem:

*Size.*—Medium. Average length 9.7 mm. Average width 2 mm.

*Color.*—2.5YR 4/6.

Flesh:

*Ripens.*—Evenly.

*Texture.*—Firm, meaty.

*Fibers.*—Few, very small, tender.

*Firmness.*—Good firmness, comparable to 'Friar' Plum (non-patented).

*Aroma.*—Slight.

*Amydgalin.*—Undetected.

*Eating quality.*—Excellent, good balance between acid and sugar.

*Flavor.*—Excellent.

*Juice.*—Moderate, enhances flavor.

*Brix.*—Average of 16°, varies slightly with number of fruit per tree and climatic conditions.

*Color.*—Varies from 5Y 8.5/8 to 5Y 8/8.

*Pit cavity.*—Color 2.5Y 6/6.

Skin:

*Thickness.*—Medium. Tenacious to the flesh.

*Texture.*—Medium. Smooth surface.

*Bloom.*—Glaucous. Moderate amount, complete coverage.

*Tendency to crack.*—None.

*Color.*—Ground color 2.5Y 8.5/6, overspread with 7.5RP 2/6 to 7.5RP 2/8. Very small, randomly spaced areas of ground color showing giving a speckled pattern.

*Astringency.*—Undetected.

Stone:

*Type.*—Clingstone.

*Size.*—Medium. Average length 22.1 mm. Average width 16.1 mm. Average thickness 12.8 mm.

*Form.*—Obovoid.

*Base.*—Varies from straight to rounded. Some stones have suture extension at base, creating beveled base.

*Apex.*—Short. Varies form acute to nearly rounded.

*Surface.*—Pitted very lightly throughout with small, sharp ridges varying in length, from base to apex. Ridges have no set pattern of number or length between stones. Some stones have small grooves on each side of suture and others are smooth.

*Sides.*—Equal to unequal. Some sides extend further outward from suture plane.

*Ridges.*—Small, narrow.

*Tendency to split.*—None.

*Color.*—10YR 8/4 when dry.

Kernal:

*Form.*—Obovoid. Round at base, acute at apex.

*Taste.*—Bitter, heavy amydgalin.

*Viable.*—Yes, embryo developed.

*Size.*—Small to medium. Average length 10.1 mm. Average width 8.8 mm. Average thickness 5.7 mm.

*Skin color.*—7.5YR 6/8, when dry.

Use: Dessert. Market — local and long distance.

Keeping quality: Good, held for 3 weeks in cold storage at 38° to 42° F. without shriveling, flesh breakdown or appreciable loss of firmness or eating quality.

Shipping quality: Good, minimal skin scarring or bruising of flesh in picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, upright growth and a productive and regular bearer of large, yellow flesh, clingstone fruit with excellent eating quality; the fruit is further characterized by having firm flesh with good storage and shipping quality and in comparison to the 'Friar' Plum (non-patented), the new fruit is more round in shape and is approximately 20 days later in maturity.

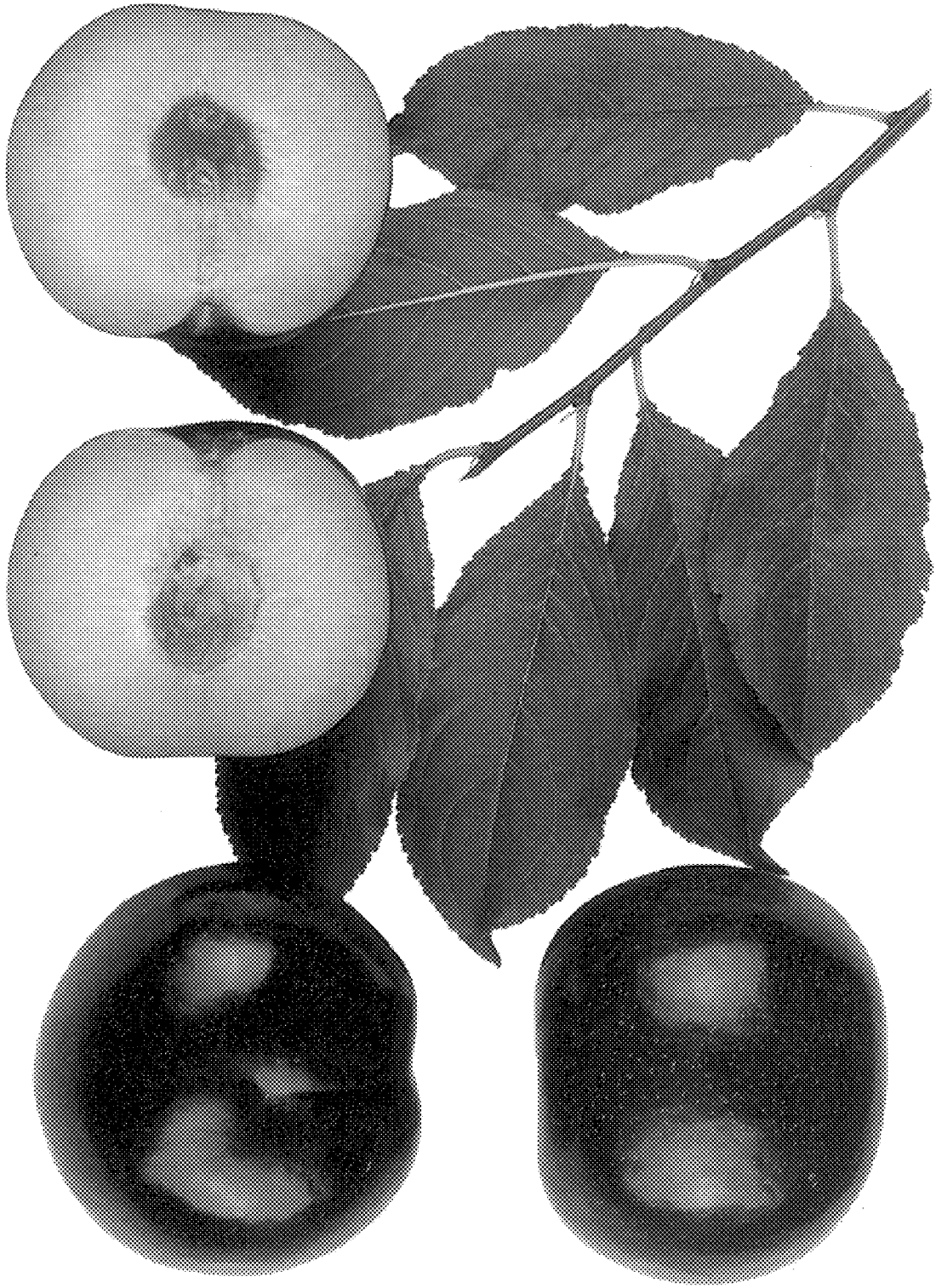

* * * * *